United States Patent [19]

Cheng

[11] Patent Number: 5,342,842
[45] Date of Patent: Aug. 30, 1994

[54] PYRIMIDONE DERIVATIVES AND ANALOGS IN THE TREATMENT OF ASTHMA OR CERTAIN SKIN DISORDERS

[75] Inventor: John B. Cheng, Waterford, Conn.

[73] Assignee: Pfizer Inc., New York, N.Y.

[21] Appl. No.: 855,046

[22] PCT Filed: Apr. 20, 1990

[86] PCT No.: PCT/US90/02162

§ 371 Date: May 8, 1992

§ 102(e) Date: May 8, 1992

[87] PCT Pub. No.: WO91/07178

PCT Pub. Date: May 30, 1991

[51] Int. Cl.$^5$ .............. A61K 31/505; A61K 31/415
[52] U.S. Cl. ...................................... 514/274; 514/395
[58] Field of Search ................................ 514/274, 395

[56] References Cited

U.S. PATENT DOCUMENTS 4,582,834  4/1986  Stenzel et al. .................. 514/274

FOREIGN PATENT DOCUMENTS 2213776   8/1974  France .
1588639   4/1981  United Kingdom .
WO8706576 11/1987  World Int. Prop. O. .

OTHER PUBLICATIONS

Patent Abstracts of Japan, vol. 10, No. 178 (C-355) [2234], Jun. 21st 1986; & JP-A-61 27 973 (Fujisawa Pharmaceut. Co.) Jul. 2, 1986.
Journal of Investigative Dermatology, vol. 84, 1985, pp. 477–482, The Williams & Wilkins Co.; K. D. Cooper et al.: "Phosphodiesterase inhibition by Ro 20-1724 reduces hyper-IgE synthesis by atopic dermatitis cells in vitro".
Journal of Investagative Dermatology, vol. 73, No. 4, 1979, pp. 261–263 The Williams & Wilkins Co.; M. A. Stawiski et al.: "Ro 201724: An agent that significantly improves psoriatic lesions in double-blind clinical trails".
Scott R. Grewe et al., "Elevated leukocyte cyclic AMP-phosphodiesterase in atopic disease: a possible mechanism for cyclic AMP-agonist hyporesponsiveness", J. Allerbgy Clin. Imnul., vol. 70, No. 6, pp. 452–457 (1982).

Primary Examiner—Zohreh Fay
Attorney, Agent, or Firm—Peter C. Richardson; Paul H. Ginsburg; Gezina Holtrust

[57] ABSTRACT

Racemic or optically active compound of the formula

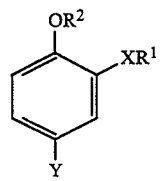

wherein X is O or NH, $R^1$ is a $(C_7-C_{11})$polycycloalkyl group, $R^2$ is methyl or ethyl, Y is

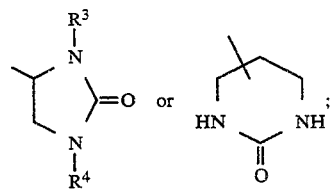

$R^3$ is hydrogen, $(C_1-C_3)$alkyl, $(C_2-C_3)$alkenyl, benzyl or phenethyl, and $R^4$ is hydrogen, $(C_1-C_3)$alkyl or $(C_2-C_3)$alkanoyl, are useful in the treatment of asthma or inflammatory airway or skin diseases.

11 Claims, No Drawings

PYRIMIDONE DERIVATIVES AND ANALOGS IN THE TREATMENT OF ASTHMA OR CERTAIN SKIN DISORDERS

BACKGROUND OF THE INVENTION

Racemic or optically active compounds of the formula (I) as defined below are useful in the treatment of asthma, or inflammatory airway or skin diseases, particularly chronic asthma, hay fever, psoriasis, atopic dermatitis and dermatitis due to contact hypersensitivity.

There is currently little useful therapy for the treatment of chronic asthma. Dexamethasone, a steriod used in such therapy, has many side effects, and there is a continuing need for therapeutic agents which, even though they may enjoy less potent activity than dexamethasone are relatively free of such side effects at dosages effective in the treatment of asthma. The same is true of atopic dermatitis, a chronically relapsing, pruritic, inflammatory skin disease, which, like asthma, generally occurs in individuals with familial history of allergic condition.

Compounds of the formula (I) and their utility as antidepressants have been recently disclosed by Saccomano et al., in published International Patent Application WO87/06576.

A particularly valuable method for the synthesis of the optically active compounds of the formula (I) wherein X is oxygen, $R^2$ is methyl, $R^1$ is exo-bicyclo[2.2.1]hept-2-yl, and Y is 3,4,5,6-tetrahydropyrimid-2(1H)-on-4-yl, which is detailed below, is also disclosed in International Patent Application No. PCT/US89/05228, filed Nov. 13, 1989.

SUMMARY OF THE INVENTION

We have now found that racemic and optically active compounds of the structural formula

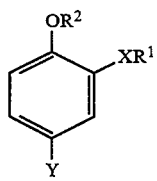

(I)

wherein
X is O or NH;
$R^1$ is a $(C_7-C_{10})$polycycloalkyl group;
$R^2$ is methyl or ethyl;
Y is

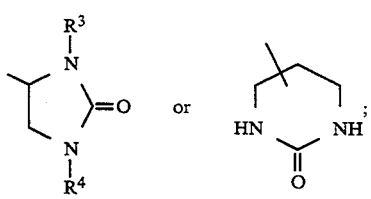

$R^3$ is hydrogen, $(C_1-C_3)$alkyl, $(C_2-C_3)$alkenyl, benzyl or phenethyl; and
$R^4$ is hydrogen, $(C_1-C_3)$alkyl or $(C_2-C_3)$alkanoyl; and the pharmaceutically acceptable salts thereof when X is NH; are valuable in the treatment of asthma and inflammatory airway and skin diseases, particularly chronic asthma, hay fever, psoriasis, atopic dermatitis and dermatitis due to contact hypersensitivity.

Exemplary of $R^1$ as $(C_7-C_{10})$polycycloalkyl are bicyclo[2.2.1]heptyl, bicyclo[2.2.2]octyl, bycyclo[3.2.1]octyl, tricyclo[5.2.1.0$^{2,6}$]decyl, and tricyclo [3.3.1.1$^{3,7}$]decyl.

The preferred compounds have $R^2$ as methyl, and X as oxygen. The more valuable compounds have Y as 3,4,5,6-tetrahydropyrimid-2(1H)-on-4-yl:

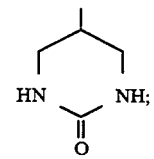

and $R^1$ as bicyclo[2.2.1]hept-2-yl:

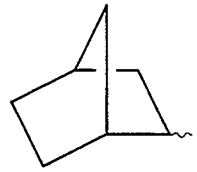

The most valuable compound of the present invention, in addition to having the preferred values of $R^2$, X and Y which are noted above, $R^1$ as exo-bicyclo [2.2.1]hept-2-yl:

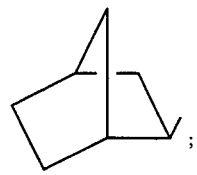

including the racemic form thereof and each of the optically active isomers which make up the racemate.

The present invention is specifically directed to pharmaceutical compositions and a method of treating humans suffering from asthma or an inflammatory airway or skin disease with a compound of the formula (I), as defined above. These compounds are particularly valuable in the treatment of chronic asthma, psoriasis and atopic dermatitis.

DETAILED DESCRIPTION OF THE INVENTION

For the purpose of treating asthma or an inflammatory disease as noted above, the compounds of the formula (I) are readily prepared by the preparative methods of Saccomano et al., cited above.

A preferred method for the synthesis of the optically active compounds of the formula (I) wherein X is oxygen $R^1$ is exo-bicyclo[2.2.1]hept-2-yl, is $R^2$ methyl and Y is 3,4,5,6-tetrahydropyrimid-2(1H)-on-4-yl is specifically exemplified below.

As noted at page 25 of patent application WO87/06576 cited above, the compounds of present utility possess in vitro activity as inhibitors of phosphodiesterases prepared from cerebral cortices of rats. More pertinent to its utility in the treatment of asthma are their activity as inhibitors of phosphodiesterases derived from guinea pig lung, as detailed below in Example 1. Utility in the treatment of asthma is further reflected by the ability of the present compounds of formula (I) to inhibit in vivo eosinophil migration into sensitized lung tissue in antigen challenged guinea pigs, as detailed in Example 2. Utility of the present compounds in dermatitis due to contact hypersensitivity is reflected by the ability of the present compounds of formula (I) to inhibit in vivo skin edema in guinea pigs sensitized to ovalbumin, as detailed in Example 3.

Furthermore, it has been demonstrated by Jon. M. Hanifin, M.D. that the leukocytes of atopic dermatitis patients have elevated phosphodiesterase (PDE) activity and consequently reduced intracellular cAMP. See Grewe et al., J. Allergy Clin. Immunol., v. 70, pp. 452–457, 1982. Exposure of the cells to a PDE inhibitor caused considerable reduction in histamine release. Similarly exposure of atopic B lymphocytes to a PDE inhibitor greatly reduced the high spontaneous IgE synthesis in mononuclear leukocyte cultures. Since both PDE inhibitors, as well as adenyl cyclase stimulators have been shown to be effective clinically (see Cooper et al., J. Invest. Dermatol., v. 84, pp. 477–482, 1985), the present compounds are also indicated for the treatment of atopic dermatitis. Dr. Hanifin has a source of human PDE isolated from mononuclear leukocyte. He was approached and readily agreed to test 5-[3-(exo-bicyclo[2.2.1]hept-2-yloxy)-4-methoxyphenyl]-3,4,5,6-tetrahydropyrimidin-2(1H)-one in his human PDE assays (see Cooper et al., cited above). Compared to Ro-20-1724 (known to have clinical utility, for example, in the treatment of psoriasis; J. Invest. Dermatol., v. 73, p. 261, 1979), the present compound showed even greater potency than Ro-20-1724 in inhibiting PDE in both the-leukocyte homogenate preparation (IC50=0.2 $\mu$M) and the intact human peripheral blood leukocyte preparation (IC50=0.3 $\mu$M).

In the systemic treatment of asthma, or an inflammatory airway or skin disease with a compound of the formula (I), the dosage is generally from about 0.01 to 2 mg/kg/day (0.5–100 mg/day in a typical human weighing 50 kg) in single or divided doses, regardless of the route of administration. Of course, depending upon the exact compound and the exact nature of the individual illness, doses outside this range will be prescribed at the discretion of the attending physician. In the treatment of asthma, intranasal (drops or spray), inhalation of an aerosol through the mouth or conventional oral administration are generally preferred. However, if the patient is unable to swallow, or oral absorption is otherwise impaired, the preferred systemic route of administration will be parenteral (i.m., i.v.), intranasal, or topical. In the treatment of inflammatory skin diseases, the preferred route of administration is oral or topical. In the treatment of inflammatory airway diseases, the preferred route of administration is intranasal or oral.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; for topical administration, in the form of solutions, gels, lotions, ointments, salves and the like, in general containing from about 0.1 to 1% (w/v) of the active ingredient; and for intranasal or inhaler administration, generally as a 0.1 to 1% (w/v) solution.

The present invention is illustrated by the following examples, but is not limited to the details thereof.

EXAMPLE 1

Inhibition of Pulmonary Phosphodiesterase (PDEIV)

Lung tissue from guinea pigs was placed in a homogenization buffer solution (20 mM Bistris, 5 mM 2-mercaptoethanol, 2 mM benzamidine, 2 mM EDTA, 50 mM sodium acetate, pH 6.5) at a concentration of 10 ml/gm of tissue. The tissue was homogenized using a Tekmar Tissumizer at full speed for 10 seconds. Phenylmethylsulfonyl fluoride (PMSF, 50 mM in 2-propanol) was added to the buffer immediately prior to homogenization to give a final PMSF concentration of 50$\mu$M. The homogenate was centrifuged at 12,000×g for 10 minutes at 4° C. The supernatant was filtered through gauze and glass wool and then applied to a 17×1.5 cm column of DEAE-Sepharose CL-6B, pre-equilibrated with homogenization buffer, at 4° C. A flow rate of 1 ml/min was used. After the supernatant had passed through the column, the column is washed with a volume of homogenization buffer at least two times that of the supernatant. PDE was eluted with a linear gradient of 0.05–0.1M sodium acetate. One hundred ×5 ml fractions were collected. Fractions were saved based on specific PDEIV activity, determined by [$^3$H]cAMP hydrolysis and the ability of a known PDEIV.

Preparation of test compounds—Compounds were dissolved in DMSO at a concentration of 10$^{-2}$M, then diluted 1:25 in water (4×10$^4$M compound, 4% DMSO). Further serial dilutions are made in 4% DMSO to achieve desired concentrations. Final DMSO concentration in assay tubes was 1%.

In triplicate, the following were added to a 12×75 mm glass tube, in order, at 0° C.: (all concentrations are given as final concentrations in assay tube)

25 $\mu$l compound or DMSO (1%, for control and blank)

25 $\mu$l assay buffer (50 mM Tris, 10 mM MgCl$_2$, pH 7.5)

25 $\mu$l [3H]-cAMP (1 $\mu$M)

25 $\mu$l PDEIV enzyme (for blank, enzyme is preincubated in boiling water bath for 10 minutes.

The reaction tubes were shaken and placed in a water bath (37° C.) for 10 minutes, at which time the reaction was stopped by placing the tubes in a boiling water bath for 2 minutes. Washing buffer (0.5 ml, 0.1M HEPES/0.1M NaCl, pH 8.5) was added to each tube in an ice bath. The contents of each tube were applied to an Affi-Gel 601 column (boronate affinity gel, 1.2 ml bed volume) previously equilibrated with washing buffer. [3H]cAMP was washed with 2×6 ml washing buffer, and [3H]5′AMP was then eluted with 6 ml 0.25M acetic acid. After vortexing, 1 ml of the elution was added to 3 ml Atomlight scintillation fluid in an appropriate vial, vortexed, and counted for [$^3$H].

Percent inhibition is determined by the formula:

$$\% \text{ inh} = 1 - \frac{\text{avg. cpm (test compound)} - \text{avg. cpm (blank (boiled enzyme))}}{\text{avg. cpm (control (no compound))} - \text{avg. cpm (blank (boiled enzyme))}}$$

IC50 is defined as that concentration of compound which inhibits 50% of specific hydrolysis of [3H]cAMP to [3H]5' AMP.

In this test, racemic 5-(3-(exo-bicyclo[2.2.1-hept-2-yloxy)-4-methoxyphenyl)-3,4,5,6-tetrahydropyrimidin-2(1H)-one demonstrated an $IC_{50}$ of 0.5 μM. In this test, substantially the same degree of activity was seen with each of the two corresponding optically active, enantiomeric compounds.

EXAMPLE 2

Inhibition of Eosinophil Migration into Sensitized Lung Tissue Challenged with Antigen in Guinea Pigs Normal Hartley guinea pigs (300–350 grams) delivered from Charles River Laboratories were housed 5–7 days before sensitization. Guinea pigs were then sensitized with 0.5 mg/kg anti-OA IgG1 or saline as control. After 48–72 hours, guinea pigs were dosed P.O. in groups of six animals each with compounds at up to 32 mg/kg using 2% Tween 80 as vehicle. After 1–1.5 hours the animals were injected i.p. with 5 mg/kg pyrilamine. Thirty minutes following pyrilamine administration, animals were exposed to 10 minutes of a 0.1% ovalbumin (OA) aerosol followed by a 15 minute cloud decay period in a Tri-R Airborne Infection Apparatus (Compression air flow =20 L/min, main air flow =8.4 L/min). Guinea pigs were removed from the apparatus and caged for 18 hours prior to sacrifice and the following lung lavage procedure.

The guinea pigs were killed with 3 ml urethane (0.5 g/ml) and the trachea was separated from the surrounding tissue. Surgical string was tied loosely aroung the trachea and an incision was made in the trachea about 1–2 cm from the thymus gland. A blunt, 15G, 1 cm feeding needle was inserted into the trachea and the string was tightened to secure the needle in place. Three × 10 ml saline was lavaged in the lungs five times. Approximately 20–25 ml was recovered and placed in a 50 ml conical tube on ice. Lavage fluid (0.475 ml) was aliquoted in a polystyrene tube containing 0.025 ml 2% Triton X-100 detergent (in duplicate).

The aliquoted sample with Triton was diluted with 1 ml PBS/0.1% Triton buffer (pH 7.0). The diluted sample (0.025 ml) was aliquoted and an additional 0.125 ml of PBS/0.1% Triton buffer was added. A colorimetric reaction was begun by adding 0.300 ml of 0.9 mg/ml o-phenylenediamine dihydrochloride (OPD) in 50mM Tris buffer/0.1% Triton (pH 8.0) plus 1 μl/ml hydrogen peroxide. After 5 minutes of incubation, 0,250 ml 4M sulfuric acid was added to stop the reaction. The O.D. of the mixture was measured at 490 nm, with background O.D. (blank tube) subtracted out.

Duplicate O.D. readings were averaged to obtain a single value for each animal. Average O.D. ± standard error is calculated using the six obtained values within each group of animals. Specific EPO response due to antigen challenge is calculated by:

1000 × [Avg O.D. (sens., challenged) −

Avg. O.D. (non-sens., challenged)]

Percent inhibition of specific EPO response due to drug pretreatment is calculated by:

$$\frac{\text{Avg O.D. (sens., drug-treated, challenged)} - \text{Avg O.D. (non-sens., challenged)}}{\text{Avg O.D. (sens., challenged)} - \text{Avg O.D. (non-sens., challenged)}} \times 100\%$$

In this test, the racemic 5-(3-(exo-bicyclo[2.2.1.]hept-2-yloxy)-4-methoxy-3,4,5,6-tetrahydropyrimidin-2(1H)-one demonstrated an ED50 of 10 mg/kg.

EXAMPLE 3

Inhibition of Skin Edema in Guinea Pigs Sensitized to Ovalbumin

Four guinea pigs (Hartley, male, 350–400 g) were sensitized with anti-ovalbumin IgG1 antibody. Two guinea pigs were orally dosed with 32 mg/Kg of the test compound and two other guinea pigs were dosed with vehicle (2% Tween-80). One-hour after dosing, each guinea pig was injected intraveneously with 1 ml of Evan Blue (7 mg/ml) and then his skin was challenged intradermally with 0.1 ml of ovalbumin (0.1%) or PBS. Twenty minutes after challenge, the skin was removed and skin edematous site (circular blue spots at challenge sites) was examined visually.

Ovalumin challenge resulted in edematous formation at the skin site challenged with ovalbumin whereas PBS challenge showed little skin edema. Both intensity and area of blue spots at antigen-challenged sites were markedly reduced in two guinea pigs dosed with racemic 5-(3-exo-bicyclo[2.2.2] hept-2-yloxy)-4-methoxyphenyl)-3,4,5,6-tetrahydropyrimidin-2(1H)-one as compared to the edema in vehicle-dosed animals.

This result demonstrates that this compound is effective against antigen-induced skin edema in guinea pigs.

EXAMPLE 4

(+)-(2R)- and (−)-(2S)-endo-Norborneol [(2R)- and (2S)-endo-Bicyclo[2.2.1]heptan-2-ol]

dl-Endonorborneol, (5.0 g, 44.6 mmol) and trichloroethyl butyrate, (5.1 g, 23.2 mmol) were dissolved in 40 ml of diethyl ether. 4A molecular sieves (4 g) were added and the mixture was stirred at room temperature. Porcine pancreatic lipase (Sigma, Type II, crude) was added portionwise in the amounts of 0.5 g, 1.0 g, 1.0 g, 1.0 g and 0.5 g at times 0, 20, 43, 50 and 67 hours, respectively. The reaction was monitored via $^1$HNMR and at approximately 50% completion (92h) filtered through diatomaceous earth and evaporated in vacuo without heat. (The alcohol sublimes easily). The crude residue was flash chromatographed on silica with a gradient eluent system of 2–25% ether/hexane to afford 2.9 g (15.9 mmol) of (2R)-endonorbornyl butyrate as a clear oil and 1.8 g (16.0 mmol) of (2S)-endonorborneol as a white solid; $[\alpha]_D = -2.03°$; e.e. 87.2% (by $^1$HNMR of derived (S)-alpha-methoxy-alpha-(trifluoromethyl)-phenylacetic acid (MTPA) ester. Because the specific rotation is so small, the e.e. values determined by NMR are a much more reliable measure of optical purity.

The recovered endonorbornyl butyrate (2.3 g, 12.6 mmole), $K_2CO_3$ (2.5 g, 18.0 mmol) and methanol (65 ml) were stirred at room temperature for 64 hours before being partitioned between diethyl ether and water. The organic portion was washed with water and brine, dried (Na$_2$SO$_4$), filtered and concentrated in vacuo to afford 1.3 g (11.6 mmol, 91.9% yield) of (2R)-endonorborneol; [alpha]$_D$ = +2.7°; e.e. 87.6% (based on $^1$HNMR of MTPA ester).

These process steps were repeated with ester exchange carried only to 44% completion to yield (2S)-endonorborneol of lower optical purity in greater than 90% yield; [alpha]$_D$ = −0.88; e.e. 71.4 (based on $^1$HNMR, as above); and (2R)-endonorborneol of higher optical purity in 56.4% yield; e.e. greater than 95% (based on $^1$HNMR as above).

EXAMPLE 5

3-[(2S)-exo-Bicyclo[2.2.1]hept-2-yloxy]-4-methoxybenzaldehyde

Diethylazodicarboxylate (28.5 g, 27.7 ml, 0.141 mol) and triphenylphosphine (36.9 g, 0.141 mol) were dissolved in 200 ml of tetrahydrofuran. To this solution was added (+)-(2R)-endo-norboreol (7.9 g., 0.0705 mol) in 100 ml of tetrahydrofuran, followed by 3-hydroxy-4-methoxybenzaldehyde (isovanillin; 21.4 g, 0.141 mol) in 100 ml of tetrahydrofuran. The resulting mixture was heated at reflux for two days, then cooled, diluted with 1.5 liters of ether, washed in sequence with half volumes of water (2×), 0.5N NaOH (2×), water and brine; dried (Na2SO4), stripped and the residue chromatographed on silica gel gradiently eluting with 0 to 10% ethyl acetate to yield 8.5 g of present title product, 8.5 g (49%), [alpha]$_D$ = +24.5° (deuterochloroform).

By the same method, (−)-(2S)-endo-norborneol was converted to 3-[(2R)-exo-bicyclo[2.2.1]hept-2-yloxy]4-methoxybenzaldehyde, identical in physical properties, except for sign of rotation.

EXAMPLE 6

3-(3-[(2S)-exo-Bicyclo[2.2.1]hept-2-yloxy]-methoxyphenyl)pentanedinitrile

Title product of the preceding Example (8.5 g, 0.0346 mol) was dissolved in 250 ml of pyridines. Cyanoacetic acid (14.6 g, 0.171 mol) and piperidine (5 ml) were added and the mixture stirred at room temperature for 4 hours, then at 60° C. for 2 hours and finally at 100° C. for 24 hours. Solvent was removed by stripping in vacuo and the residue was taken up in 250 ml ethyl acetate, washed with saturated NaHCO$_3$ and then water, restripped and crystallized from isopropyl alcohol/isopropyl ether to yield 5.84 g (54%) of present title product; m.p. 121°–123° C.; [alpha]$_D$ = +17.8° (deuterochloroform).

By the same method, the entiomeric product of the preceding Example was converted to 3-(3-[(2R)-exo-bicyclo[2.2.1]hept-2-yloxy]-4-methoxyphenyl)pentanedinitrile, having identical physical properties except for sign of rotation.

EXAMPLE 7

3-(3-[(2S)-exo-Bicyclo[2.2.1]hept-2-yloxy]-4-methoxyphenyl)glutaramide

To title product of the preceding Example (5.82 g, 0.0188 mol) in 150 ml of 2:1 acetone:H$_2$O by volume was added 5 ml 10% Na$_2$CO$_3$ followed by the dropwise addition of 30% H$_2$O$_2$ (8 ml, 0.094 mol) maintaining a temperature of 0°–5° C. After stirring for 16 hours at room temperature, the mixture was poured into water (300 ml) and ethyl acetate (500 ml) and the mixture stirred for 1 hour to dissolve all solids. The organic layer was separated, washed with H20 and the brine, dried and stripped to a crystalline residue which was flash chromatographed on silica gel using 15:1 CH$_2$Cl$_2$CH$_3$OH as eluant to yield 3.7 g of present title product, m.p. 198.5°–199.5° C.; ir (KBr) cm$^{-1}$ 3335, 3177, 2952, 1674, 1631, 1516, 1406, 1256, 1142, 1003, 809, 685, 641 cm$^{-1}$.

By the same method, the enantiomeric product of the preceding Example was converted to 3-(3-[(2R)-exo-bicyclo[2.2.1]hept-2-yloxy]-4-methoxyphenyl)-glutaramide, having the same physical properties, except for sign of rotation.

EXAMPLE 8

5-(3-[(2S)-exo-Bicyclo[2.2.1.]hept-2-yloxy]-4-methoxyphenyl)-3,4,5,6-tetrahyropyrimidin-2(1H)-one To title product of the preceding Example (3.7 g, 0.0107 mol was dissolved in 250 ml of pyridine was added lead tetraacetate (10.92 g, 0.0246 mol) in 250 ml of pyridine. After stirring for 30 hours, the reaction was stripped in vacuo, and the oily residue taken up in 100 ml CH$_2$Cl$_2$, washed with H$_2$O and the brine, dried (Na$_2$SO$_4$), stripped, and the resulting solids triturated with ether to yield present title product as a white solid, 1.21 g; m.p. 202°–203° C.; [alpha]$_D$ = +14.45° (deuterochloroform).

By the same method, the enantiomeric product of the preceding Example was converted to 5-(3-(2R)-exo-bicyclo[2.2.1]hept-2-yloxy]-4-methoxyphenyl)-3,4,5,6-tetrahydropyrimidin-2(1H)-one, having the same physical properties except for sign of rotation.

I claim:

1. A method for relieving skin disease in a human which comprises administering to said human an asthma, airway or skin inflammation relieving amount of an optically active or racemic compound having the formula

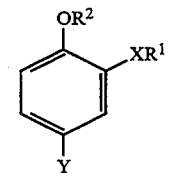

(I)

wherein R$^1$ is a polycycloalkyl group having from 7 to 11 carbon atoms;
R$^2$ is methyl or ethyl;
X is O or NH;
Y is

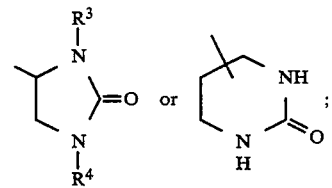

R$^3$ is hydrogen, (C$_1$–C$_3$) alkyl, (C$_2$–C$_3$) alkenyl, benzyl or phenethyl; and
R$^4$ is hydrogen, (C$_1$–C$_3$) alkyl or (C$_2$–C$_3$) alkanoyl;
or a pharmaceutically acceptable acid addition salt thereof when X is NH.

2. A method of claim 1 wherein R² is methyl and X is O.

3. A method of claim 2 wherein Y is

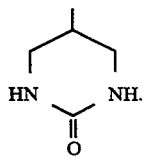

4. A method of claim 3 wherein R¹ is bicyclo[2.2.1]hept-2-yl.

5. A method of claim 4 wherein R¹ is exo-bicyclo[2.2.1]hept-2-yl.

6. A method of claim 5 wherein the compound is racemic.

7. A method of claim 5 wherein the compound is optically active.

8. A method of claim 1 for the relief of psoriasis.

9. A method of claim 5 for the relief of psoriasis.

10. A method of claim 1 for the relief of atopic dermatitis.

11. A method of claim 5 for the relief of atopic dermatitis.

* * * * *